United States Patent
Riedel et al.

(10) Patent No.: US 11,738,979 B2
(45) Date of Patent: Aug. 29, 2023

(54) ARRANGEMENT FOR DISINFECTING CAN LIDS FOR CLOSING CANS

(71) Applicants: KHS GMBH, Dortmund (DE); CLARANOR SA, Avignon (FR)

(72) Inventors: Christophe Riedel, Avignon (FR); Ludwig Cluesserath, Bad Kreuznach (DE)

(73) Assignees: KHS GmbH, Dortmund (DE); Claranor SA, Avignon (FR)

(*) Notice: Subject to any disclaimer, the term of this patent is extended or adjusted under 35 U.S.C. 154(b) by 80 days.

(21) Appl. No.: 17/473,395

(22) Filed: Sep. 13, 2021

(65) Prior Publication Data

US 2021/0403302 A1 Dec. 30, 2021

Related U.S. Application Data

(63) Continuation-in-part of application No. 16/085,667, filed as application No. PCT/EP2017/051459 on Jan. 25, 2017, now abandoned.

(30) Foreign Application Priority Data

Mar. 16, 2016 (DE) .................... 10 2016 104 859.3

(51) Int. Cl.
*B67B 3/00* (2006.01)
*B67B 3/06* (2006.01)
*A61L 2/10* (2006.01)

(52) U.S. Cl.
CPC ............. *B67B 3/003* (2013.01); *B67B 3/06* (2013.01); *A61L 2/10* (2013.01); *B67B 2201/06* (2013.01)

(58) Field of Classification Search
CPC ....... B67B 3/003; B67B 3/06; B67B 2201/06; A61L 2/10; A61L 2/26; A61L 2/087
See application file for complete search history.

(56) References Cited

U.S. PATENT DOCUMENTS

| | | | |
|---|---|---|---|
| 3,018,184 A | 1/1962 | Martin | |
| 3,330,403 A | 7/1967 | Greck | B65G 47/14 |
| | | | 198/392 |
| 3,527,017 A | 9/1970 | Bott | B67B 1/005 |
| | | | 53/500 |
| 4,981,649 A | 1/1991 | Shibauchi | B65B 7/2807 |
| | | | 141/63 |
| 4,987,721 A | 1/1991 | Turtschan | |

(Continued)

FOREIGN PATENT DOCUMENTS

| | | |
|---|---|---|
| DE | 3900448 A1 | 7/1990 |
| DE | 68907508 T2 | 2/1994 |

(Continued)

OTHER PUBLICATIONS https://allstatecan.com/products product listing as of May 7, 2021. (Year: 2021).

*Primary Examiner* — Sean M Luck
(74) *Attorney, Agent, or Firm* — Laurence A. Greenberg; Werner H. Stemer; Ralph E. Locher

(57) ABSTRACT

An arrangement for disinfecting can lids (32) and for closing cans includes a feed device (12) which feeds a can closing unit (24). Receiving portions (30) for individual can lids (32) are arranged in the feed device (12). The feed device (12) is situated in the feed region of the can closing unit (24). At least one sterilization device (18, 20), for can lids (32) received individually in the feed device (12), is arranged in a conveying region of the feed device.

14 Claims, 2 Drawing Sheets

(56) References Cited

U.S. PATENT DOCUMENTS

| | | | |
|---|---|---|---|
| 5,076,039 A | 12/1991 | Shibauchi et al. | |
| 8,884,249 B2 | 11/2014 | Drenguis | |
| 9,107,968 B2 | 8/2015 | Knott et al. | |
| 2006/0225837 A1 | 10/2006 | Haase | B65B 55/10 156/281 |
| 2011/0142731 A1 | 6/2011 | Beckmann | A61L 2/208 422/292 |
| 2013/0161532 A1 | 6/2013 | Naka | A61L 2/087 250/455.11 |
| 2014/0027651 A1 | 1/2014 | Kawasaki | A61L 2/08 250/453.11 |
| 2015/0246801 A1 | 9/2015 | Niehr | A61L 2/20 422/28 |

FOREIGN PATENT DOCUMENTS

| | | |
|---|---|---|
| DE | 102013103259 A1 | 10/2014 |
| EP | 1518565 A1 | 3/2005 |
| EP | 2650022 A1 | 10/2013 |
| GB | 1093751 A | 12/1967 |
| JP | S5991959 A | 5/1984 |
| JP | H04242525 A | 10/2006 |
| WO | 2005005260 A1 | 1/2005 |
| WO | 2012069101 A1 | 5/2012 |

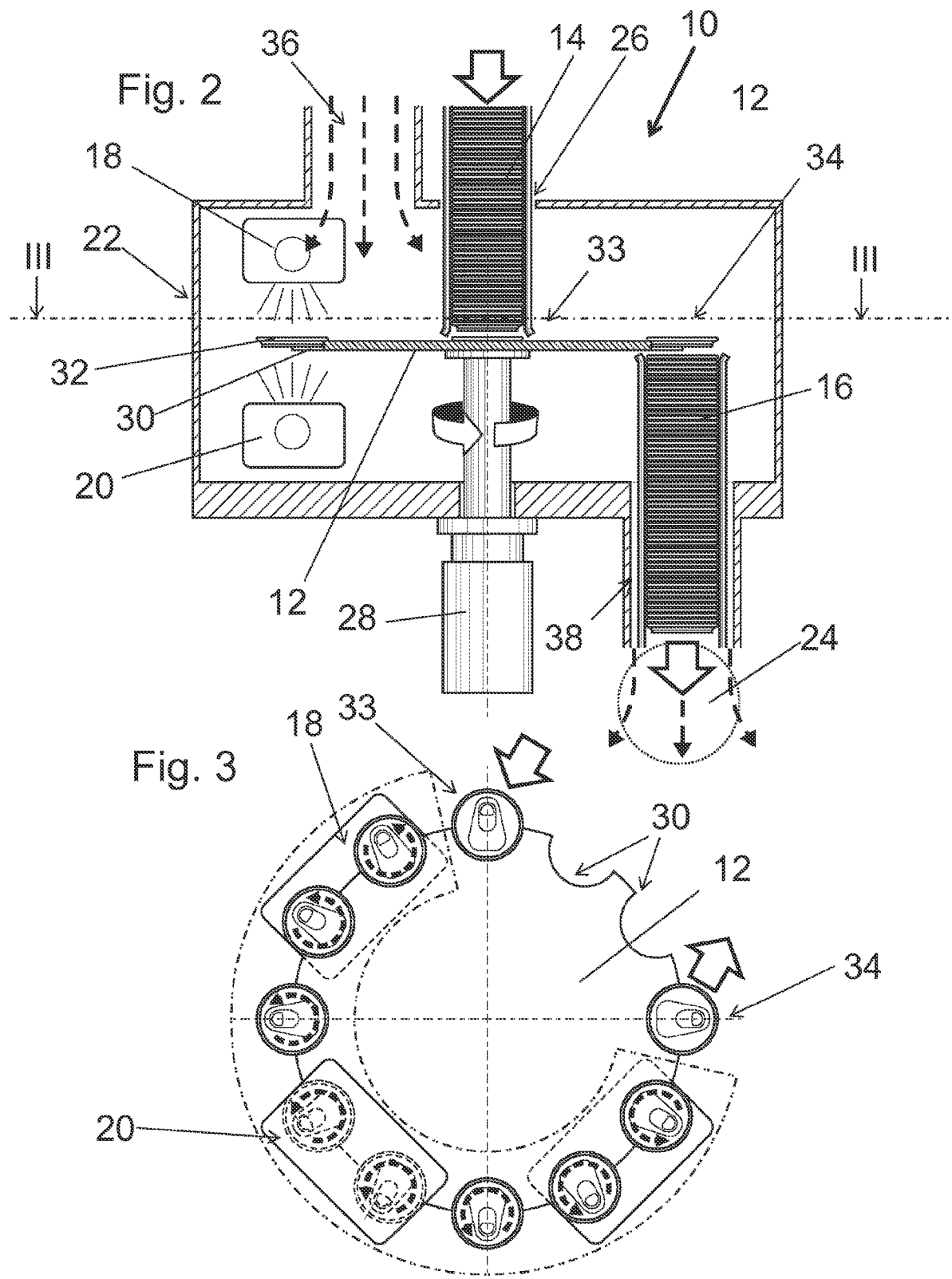

ARRANGEMENT FOR DISINFECTING CAN LIDS FOR CLOSING CANS

CROSS-REFERENCE TO RELATED APPLICATION

This application is a continuation in part of patent application Ser. No. 16/085,667, filed Sep. 17, 2018; which was a § 371 national stage filing of international application No. PCT/EP2017/051459, filed Jan. 25, 2017, which designated the United States; this application also claims the priority, under 35 U.S.C. § 119, of German patent application No. DE 10 2016 104 859.3, filed Mar. 16, 2016; the prior applications are herewith incorporated by reference in their entirety.

FIELD AND BACKGROUND OF THE INVENTION

The present invention relates to an arrangement for disinfecting can lids and for closing cans. Separate devices arranged at different positions of a filling plant for the containers have hitherto been provided by prior art to perform this task. A problem with these known arrangements is that the sterilized can lids have to be transported from the sterilization unit to a closing unit. During transport, the can lids have to be kept sterile until they are fed to the can closing unit. Their path must therefore be enclosed and if necessary a corresponding sterile or sterilizing gas supply in overpressure from the seamer down to the sterilization treatment must be provided in the transport region to prevent bacteria from reaching the can lids through the surrounding air. A clean room is necessary if an enclosed arrangement is not possible. Additionally, a buffer system is needed to balance different working cycles and output rates of the separate units. If a problem occurs in the closing unit, already disinfected can lids have to be stored under sterile conditions, e.g. in a clean room. The risk of re-contamination of the sterilized can lids due to remaining intact germs after sterilization or due to germs of the surroundings grows with residence time between sterilization of the can lid and closure of the can.

SUMMARY OF THE INVENTION

It is therefore the object of the invention to create an arrangement in which the sterility of the can lids, and in particular can lids of aluminum before they are closed is more effectively ensured.

This object is inventively resolved by an arrangement as claimed. Advantageous further embodiments of the invention are the subject-matter of the dependent claims. Further advantages and features of this aspect of the invention can be taken from the general description and the description of the exemplary embodiment.

According to the invention, the arrangement comprises a feed device, e.g. a transport star wheel, in which receiving portions, e.g. transport recesses, are arranged for individual can lids. The feed device is arranged (directly) in the feed region of a can closing unit. According to the invention the arrangement comprises at least one sterilization device for the can lids received individually in the feed device, the sterilization device being arranged in the conveyor region of the feed device.

The advantage of the invention is that the sterilization device is arranged directly in connection with the feed device for the can closing unit. As a result, the sterilized can lids can be supplied preferably without connecting conveyor path to the can closing unit. At least the single and individual sterilized can lids move over only a minimal connecting conveyor path before being fed, in particular from the feed device, to the can closing unit.

The can lids are preferably singularized and/or in particular individually separated and sterilized. The can lids are transported advantageously individually through the sterilization device without contacting each other. Preferably, one can lid after another is transported through the arrangement so that a working cycle and in particular an output rate can be controlled precisely and synchronized to a working cycle of the can closure unit. Especially, a working cycle and an output rate of the sterilization device and/or the feed device can be directly coupled to a working cycle of the can closure unit. A buffer storage is preferably not necessary. Advisably, a risk of re-contamination is minimized. The sterility of the can lids before they are closed is in particular more effectively ensured.

Preferably, the arrangement can work basically independent of a room cleanness. In particular, a clean room is not necessary for the supply of the sterile cans lids to the can closing unit as the sterile can lids are just handled over to the can closing unit.

Preferably, a can lid for the purpose of this application comprises a flat, in particular cylindrical, body. Appropriately, a height of the can lid is much smaller than the diameter of the can lid. In particular, a height to diameter ratio is at least between 1/3 and 1/30. Preferably the height to diameter ratio is at least between 1/5 and 1/20. Advantageously, the height to diameter ratio is about 1/10 (+−50%). A diameter can be especially about between 30 mm and 150 mm. In addition, larger diameters of the can lids may be possible. Preferably a can lid is (at least party) rotationally symmetric. In particular, can lids can be stacked on one another, i. e. with an appropriate horizontally arranged diameter. A can lid is appropriately made of a thin sheet metal, like aluminum, with a thickness in between 0.05 mm and 20 mm. Preferably a thickness of a can lid is between 0.2 mm and 10 mm. Preferably, the can lid comprises a circumferential border with a least collar-like part. Preferably, the collar-like part spreads in radial growing direction. Especially, the collar-like part can comprise at least partially e.g. an I-shaped, z-shaped and/or C-shaped cross-sectional development. Advantageously, the collar-like part can comprise a sealing area. In particular, the can lid can contact a can at least at the sealing area. In particular, the collar-like part is mechanically robust so that the can lid can be manipulated along the collar-like part.

The sterilization device preferably contains a sterilizer, e.g. UV emitter, for the top and for the underside of the lid respectively. Separate sterilizers for top and underside advantageously allow a static arrangement of the sterilizers and a fast sterilization procedure. In particular, sterilizers do not have to be moved around relative to the can lids. A fast sterilization can be guaranteed. Advantageously UV-emitters allow to short sterilization time. An effective sterilization time is in particular much shorter than the time that is necessary for movement of the can lids through the sterilization device. In this way the can lid is sterilized on both sides, although as a minimum requirement it would be sufficient for the can lid to be sterilized only on its underside facing the can because this affects the hygiene of the product filled into the can, for example a beverage. Alternatively, the sterilization device can of course also work with gas, chemicals and/or heat. The use of a UV emitter least affects the overall technical design of the inventive arrangement.

The feed device is preferably configured as a transport star wheel which in its rotary motion is controlled in particular by a motor. A transport star wheel is technically simple to realize and ensures a safe pick-up and feeding of the can lids to the can closing unit, and the transport star wheel also comprises enough space on its periphery for the arrangement of the at least one sterilization device. In particular, the transport star wheel is arranged horizontally and rotates about a (basically) vertical axis. Advantageously a can lid is taken up in a separate recess of the transport star wheel, moved through the sterilization device and unloaded. In particular, a horizontal movement is comfortable to realize due to the mechanical structure of the can lids. Advantageously, a working cycle of the transport star wheel is easily adapted with the speed of rotation to match a working cycle of the can closing unit.

Preferably the sterilization device is arranged on the peripheral section of the transport star wheel. The sterilization device is therefore able to disinfect or sterilize the can lids as they pass on the circumference of the transport star wheel. The can lids can pass at a short distance. A high intensity of the UV emitter can be guaranteed. A distance of an UV emitter to a can lid can be smaller than half the diameter of a can lid.

The can closing unit is preferably arranged in the conveyor region of the transport star wheel so that the sterilized can lids are transferred directly from the feed star wheel and in particular the transport star wheel, to the closing position of the can closing unit. Advantageously, there is no conveyor path between the sterilization device and the closing unit. Preferably, the sterilization device can be arranged nearer to a discharge position than to an feed position. In particular, a transport length of the sterilized can lid is in particular therefore reduced to a certain sector of the transport star wheel. So, the can lids are preferably sterilized just before they are discharged from the transport star wheel to the closing position of the can closing unit. A residence time of the sterile can lid can be reduced to at least less than 60 seconds or even a few 10 seconds or even less. In a particular case, the residence time of a sterilized can lid between the sterilization device and the closure of the can is about less than 10 seconds. This facilitates a high sterility of the can lid when it is closed. Preferably, re-contamination practically cannot take place in such short period of time. This can be even better guaranteed, if during the time between sterilization star wheel and closing position lids are restacked, and thus, the sensitive surface of the lid is not exposed to outer air. Clean room conditions of the surroundings are not necessary.

On its peripheral section the feed star wheel preferably includes transport recesses for the individual can lids and/or singly separated can lids, said recesses forming the receiving portions for the can lids. The receiving portions span about at least a reasonable circumferential angle of the can lid so that a secure handling of the can lid is guaranteed. In particular, a circumferential angle of a span at least a part of the receiving portions is between 90° and 180°. Advantageously, the can lids can just slide in and out of the receiving portions in a radial direction. Advantageously, the can lids can be taken up in the recess. Especially, at least the edge of a can lid can be taken up at the recess. Advisably the can lids can be hung into a recess. An arrangement of this kind is easy to realize and ensures a more secure holding of the can lids during their sterilization and, if applicable, when they are applied to the can in the can closing unit. Advantageously, a top surface and/or a bottom surface of the can lid are freely, and preferably optically, accessible for sterilization. In particular there is no relative movement between the recess and a taken up can lid, i. e. the can lid does preferably not move relative to the recess during transportation. Preferably, a sealing surface of the can lid is not mechanically stressed and especially scratches due to a relative movement are avoided. So can lids can preferably also be easily transferred from a stacker device onto the transport star wheel and/or from the transport star wheel to a stacker device.

The sterilization device preferably contains at least one pulsed light device which contactlessly irradiates the lids using powerful light pulses, preferably in the UV range, at the areas to be sterilized and thus ensures sterility. The advantage of such a sterilization device is also that they in no way impede the progress and transport of the individual can lids in the transport star wheel to the closing unit or e.g. a second (downstream) stacker device. Advantageously, the necessary period for sterilization with a pulsed light device is short. Preferably, the period is (much) shorter than the period for transport through the sterilization device. A sterilization time is at least less than a second and preferably less than a few 10 ms. In particular, a sterilization time can be about 0.3 ms (+−50%) or even less. Advantageously, the sterilization process can therefore be subordinated to the transport through the sterilization device. A big advantage is that a period of a working can be subordinated to the working cycle of a can closing unit so that sterile preferably can lids can be delivered to the closing unit.

A first stacker device for can lids is preferably arranged in the entry of the feed device so that the can lids can be transferred individually from the first stacker device to the transport star wheel.

In an advantageous embodiment of the invention a second stacker device which lies within the feed of the can closing unit is arranged at the exit from the feed device, e.g. the transport star wheel. In particular, the second stacker device can take up a few or preferably even several can lids. In this case the second stacker device preferably forms the feed to the can closing unit. This also permits a very direct feed of the sterilized can lids to the can closing unit, the advantage of this arrangement being that the second stacker device arranged between the feed device and the can closing unit forms a buffer so that even shortest-term variations in the sterilization and/or operating speed of the can closing units can be balanced out, limited of course by the stacking capacity of the second stacker device.

The can closing unit is preferably arranged directly in or at the exit from the feed device so that the can lids are especially not required to traverse (long) conveying paths once they have been discharged from the feed device.

In an advantageous embodiment of the invention, the can closing unit is arranged directly at the feed device and the feed device feeds the sterilized can lids individually to the can closing unit. Preferably, the lid sterilization unit can be incorporated into the can closing unit. In this case the feed device can already act advantageously as a descrambling device for the feed to the can closing unit. Sterile can lids preferably can be supplied to the can closing unit directly and in particular on demand of the can closing unit. Thus the feed device fulfils two tasks at the same time, namely the separating out and sterilizing of the can lids, and feeding them into the can closing unit.

The feed device and the sterilization device are preferably arranged in a sealed housing which comprises a supply and a discharge for a sterile or sterilizing gas and of course a feed opening and a discharge opening for the can lids. In this way the entire process can be carried out in a sterile space, thereby increasing the sterility of the can lids to be fitted in the can closing unit.

In an advantageous embodiment of the invention the first stacker device is arranged in the feed opening and/or the second stacker device is arranged in the discharge opening. This creates a lot of space in the housing and allows a simple feeding and removing of the can lids.

The openings which are provided for the feeding or removing of the can lids are preferably also used for gas feeding and removing. In this way the number of openings in the otherwise sealed housing can be minimized, thereby enhancing the maintenance of sterility. However it is not absolutely necessary for the feed opening for the can lids to be used as the feed opening for the gas as well.

The following terms are used synonymously: gas feed—gas feed channel; can lids—lids; outlet pipe—gas discharge—can lid discharge opening; sterilization device—sterilizer—UV emitter It will be apparent to the skilled person that the above embodiments of the invention can be combined with one another in any desired way.

The invention is now described by reference to an exemplary embodiment in conjunction with the schematic drawings, in which

BRIEF DESCRIPTION OF THE SEVERAL VIEWS OF THE DRAWING

FIG. 2 shows a vertical section through the arrangement of FIG. 1, and

FIG. 3 shows a section III-III from FIG. 2.

DESCRIPTION OF THE INVENTION

Figure 1:
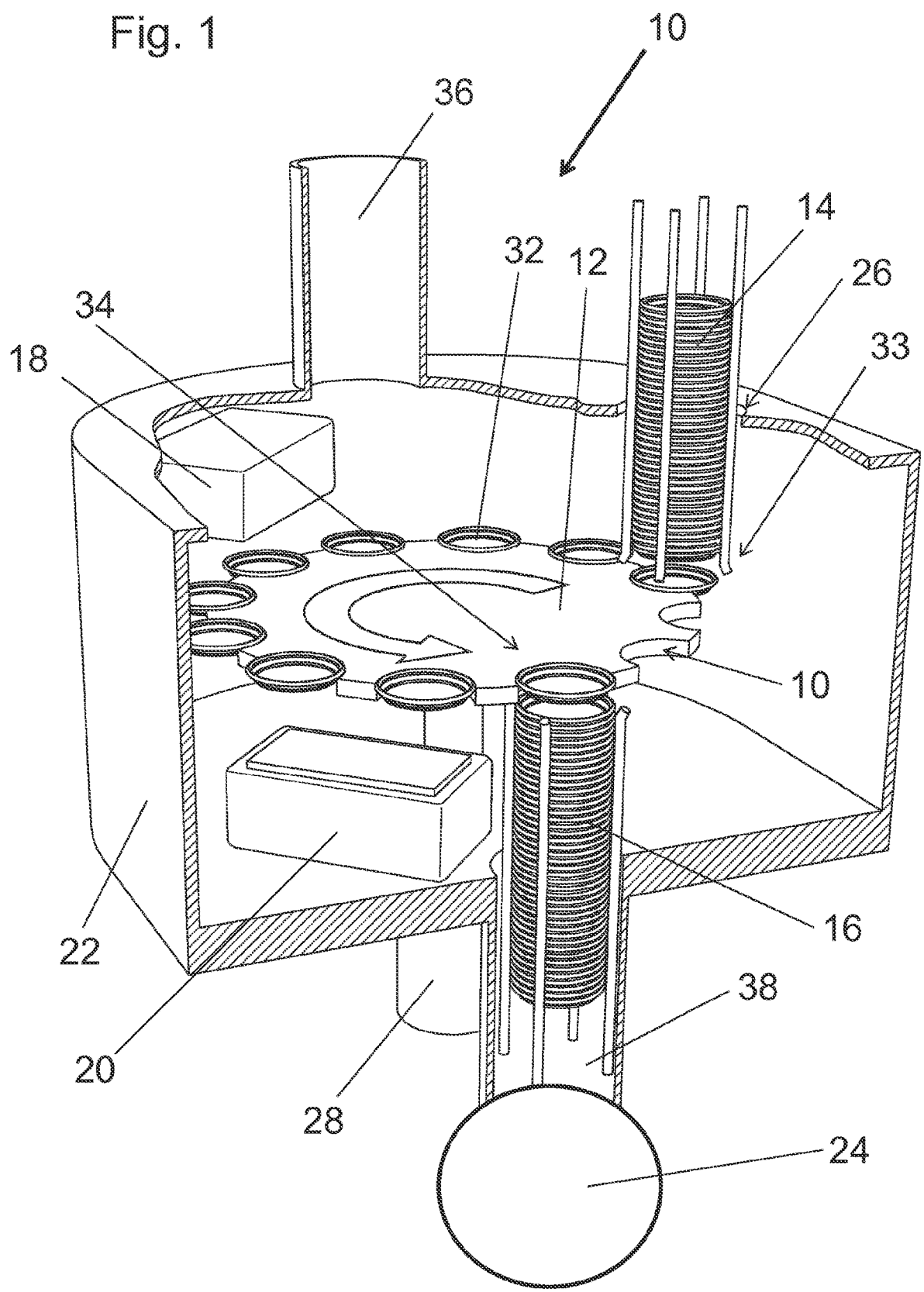
FIG. 1 shows a perspective view of an inventive arrangement having a stacker device arranged between the feed device and the can closing unit.

According to FIGS. 1 to 3, the inventive arrangement 10 comprises a feed device 12 in the form of a transport star wheel driven by a motor 28. The transport star wheel 12 is arranged together with a first stacker device 14, a second stacker device 16, an upper UV emitter 18 and a lower UV emitter 20 in a substantially sealed housing 22. The first stacker device 14 is arranged in a feed opening 26 of the housing 22. The second stacker device 16 is arranged in an outlet pipe 38 which projects out of the housing 22. The outlet pipe 38 also forms a gas discharge for a process gas used in the housing 22, e.g. a sterile or sterilizing purging gas. A can closing unit 24 is arranged at the exit from the second stacker device 16.

Around its periphery, the transport star wheel 12 has transport recesses 30 in which individual can lids 32 are accommodated and hung into the respective recesses. The direction of rotation of the transport star wheel 12 is indicated by an arrow. The gas feed and the discharge 36, 38 can be provided optionally. The housing is preferably completely sealed except for the feed opening 26 for the can lids, the gas feed channel 36 and the outlet pipe 38 which forms both the can discharge opening and the gas discharge. Clean room conditions of the surroundings are not necessary.

The inventive arrangement works as follows:
The can lids 32 are fed to the transport star wheel 12 via the first stacker device 14 at the feed point 33. At the exit of the first stacker device 14 is arranged a descrambling device (not shown) which feeds the can lids 32 individually to the transport star wheel, i.e. to the transport recesses of the transport star wheel 12. The can lids 32 are hung into the recess 30 of the transport star wheel 12. The lids are then transported in the transport recesses 30 of the transport star wheel 12, passing along beneath the upper UV emitter 18 and above the lower UV emitter 20 so that the can lids 32 are sterilized both on their upper and on their lower side. The lower UV emitters 20 near to the discharge point 34 than to the feed point 33. So the sterilized can lids 32 do only need to be transported along a certain sector of the transport star wheel 12. Finally, at the discharge point 34 the can lids are fed to the second stacker device 16 which forms the feed device for the closing unit 24 arranged beneath it. A gas, in particular a sterile or a sterilizing gas, which is discharged at the outlet pipe 38 in which the second stacker device 16 is arranged, is also fed to the housing 22 through the gas feed channel 36. In this way, a sterile or sterilizing gas is washed over and around the can lids 32 during the entire descrambling, sterilization and feeding process so that the sterility produced by the UV emitters 18, 20 is maintained until the closing of a can with a sterilized can lid 32 in the can closing unit 24. Clean room conditions of the surroundings are not present as they are not necessary.

The dashed arrows in FIG. 2 indicate the path of the sterile gas which can be for example oxygen or CO2 or any desired sterile or sterilizing gas.

The invention is not confined to the depicted exemplary embodiment but is capable of variation within the scope of the following claims.

The following is a summary list of reference numerals and the corresponding structure used in the above description of the invention:

LIST OF REFERENCE CHARACTERS

10 Arrangement for disinfecting can lids and for closing cans
12 Feed device—transport star wheel
14 First stacker device
16 Second stacker device
18 Upper UV emitter—first sterilization device
20 Lower UV emitter—second sterilization device
22 Housing
24 Can closing unit
26 Feed opening for can lids
28 Drive motor
30 Transport recess in the transport star wheel for individual can lids
32 Can lids
33 Feed point of the conveyor path
34 Discharge point of the conveyor path
36 Gas feed channel
38 Outlet pipe

The invention claimed is:

1. An arrangement for disinfecting can lids and for closing cans, the arrangement comprising:
   a feed device for conveying can lids in a conveyor region over a conveyor path from a feed point of the conveyor path to a discharge point of the conveyor path, said feed device including a transport star wheel formed with receiving recesses for holding individual can lids;
   said feed device being arranged in a feed region of a can closing unit;
   a first stacker device arranged at the feed point of the conveyor path for transferring can lids individually to said transport star,
   a second stacker device arranged at the discharge point of the conveyor path and in the feed region of the can closing unit, said second stacker device for receiving can lids from the transport star, and at least one sterilization device for the can lids that have been received individually in said receiving pockets, said sterilization device being arranged in a conveying region of said feed device, said sterilization device having a pulsed light device for irradiating light pulses in the UV range disposed above and below said transport star wheel the light pulses for contactless irradiation of individual lids received in the receiving recesses of the transport star wheel, the light pulses ensuring sterility of the can lids.

2. The arrangement according to claim 1, wherein said pulsed light device includes UV emitters for sterilizing the top and the underside of the individual can lids.

3. The arrangement according to claim 1, wherein said receiving recesses are formed in a peripheral section of said transport star wheel.

4. The arrangement according to claim 3, wherein said transport star wheel rotates about a vertical axis of rotation.

5. The arrangement according to claim 3, wherein said recesses are configured for hanging a can lid therefrom.

6. The arrangement according to claim 3, wherein said sterilization device is arranged at the peripheral section of said transport star wheel.

7. The arrangement according to claim 3, wherein said sterilization device is arranged closer to a discharge position of said transport star wheel than to a feed point of said transport star wheel.

8. The arrangement according to claim 1, wherein said pulsed light device is a UV radiator.

9. The arrangement according to claim 1, wherein said second stacker device defines a feed of the can closing unit.

10. The arrangement according to claim 1, wherein the can closing unit is disposed directly in or at a discharge of said feed device.

11. The arrangement according to claim 1, wherein the can closing unit is disposed on said feed device and said feed device is configured to individually feed sterilized can lids to the can closing unit.

12. The arrangement according to claim 1, further comprising a sealed housing enclosing said feed device and said sterilization device, said sealed housing being formed with a gas feed and a gas discharge for a sterile gas, and with feed and discharge openings for the can lids.

13. The arrangement according to claim 12, wherein said feed opening for the can lids and said gas feed and/or said discharge opening for the can lids and said gas discharge are integrated.

14. The arrangement according to claim 12, wherein the second stacker device disposed in said gas discharge.

* * * * *